(12) United States Patent
Koelker et al.

(10) Patent No.: US 11,969,245 B2
(45) Date of Patent: Apr. 30, 2024

(54) ANALYTE MEASURING PATCH

(71) Applicant: Roche Diabetes Care, Inc., Indianapolis, IN (US)

(72) Inventors: Karl-Heinz Koelker, Gruenstadt (DE); Frederic Wehowski, Hockenheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 218 days.

(21) Appl. No.: 16/074,920

(22) PCT Filed: Mar. 9, 2017

(86) PCT No.: PCT/EP2017/055504
§ 371 (c)(1),
(2) Date: Aug. 2, 2018

(87) PCT Pub. No.: WO2017/153506
PCT Pub. Date: Sep. 14, 2017

(65) Prior Publication Data
US 2019/0029577 A1 Jan. 31, 2019

(30) Foreign Application Priority Data

Mar. 11, 2016 (EP) ..................................... 16159883

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0531* (2013.01); *A61B 5/14546* (2013.01);
(Continued)

(58) Field of Classification Search
None
See application file for complete search history.

(56) References Cited

U.S. PATENT DOCUMENTS 6,459,335 B1 10/2002 Darmawaskita et al.
6,908,536 B2 6/2005 Beckmann
(Continued)

FOREIGN PATENT DOCUMENTS

CN 1735375 A 2/2006
CN 101005798 A 7/2007
(Continued)

OTHER PUBLICATIONS

Chinese Patent Application 201780016577.3 First Office Action (translated) dated Jul. 21, 2020. 4 pages.
(Continued)

*Primary Examiner* — Alex M Valvis
*Assistant Examiner* — Aurelie H Tu
(74) *Attorney, Agent, or Firm* — Woodard, Emhardt, Henry, Reeves & Wagner, LLP (57) ABSTRACT

Disclosed is an analyte measuring patch for invasive measuring a concentration of an analyte, in particular glucose. The analyte measuring patch includes a sensor with a working electrode (101), a counter electrode (103) and a reference electrode 102). The patch further includes an electronics unit with a microcontroller (1200) and a current measurement unit. The microcontroller (1200) includes a control output (DAC), a first analogue input (ADC-1) and a second analogue input (ADC-2). The control output (DAC) is operatively coupled with a control electrode, the control electrode being either of the working electrode or (101) or the counter electrode (103). The first analogue input (ADC-2) is operatively coupled with a measurement electrode via the current measurement unit, the measurement electrode being either of the working electrode (101) or the counter electrode (103). The second analogue input (ADC-1) is operatively coupled with the reference electrode (102). The microcontroller (1200) is configured to control, by providing
(Continued)

a control voltage to the control output (DAC), a potential difference between the working electrode (101) and the counter electrode (103) to equal a predefined polarization voltage.

20 Claims, 6 Drawing Sheets

(51) Int. Cl.
    *A61B 5/0531*     (2021.01)
    *A61B 5/1486*     (2006.01)
    *A61B 5/15*     (2006.01)
    *A61B 5/021*     (2006.01)

(52) U.S. Cl.
    CPC .... *A61B 5/14865* (2013.01); *A61B 5/150969* (2013.01); *A61B 5/7225* (2013.01); *A61B 5/02141* (2013.01); *A61B 2560/045* (2013.01)

(56) References Cited

U.S. PATENT DOCUMENTS

| | | | |
|---|---|---|---|
| 8,548,552 B2 | 10/2013 | Tsoukalis | |
| 2005/0247576 A1 | 11/2005 | Tom et al. | |
| 2008/0000779 A1 | 1/2008 | Wang et al. | |
| 2008/0156661 A1* | 7/2008 | Cooper | A61B 5/6848 205/775 |
| 2008/0319296 A1* | 12/2008 | Bernstein | A61B 5/14865 600/365 |
| 2009/0054737 A1* | 2/2009 | Magar | A61B 5/0404 600/300 |
| 2009/0057148 A1* | 3/2009 | Wieder | A61B 5/14532 204/403.01 |
| 2009/0076360 A1* | 3/2009 | Brister | G16Z 99/00 600/365 |
| 2010/0066378 A1 | 3/2010 | Ahmadi et al. | |
| 2010/0198034 A1 | 8/2010 | Thomas et al. | |
| 2011/0257495 A1* | 10/2011 | Hoss | A61B 5/14532 600/347 |
| 2012/0199496 A1* | 8/2012 | Sekimoto | A61B 5/14532 205/775 |
| 2012/0205258 A1 | 8/2012 | Noble et al. | |
| 2012/0245438 A1* | 9/2012 | Bernini | A61B 5/0031 600/309 |
| 2013/0041242 A1* | 2/2013 | Karlsson | A61B 5/7445 600/365 |
| 2013/0184546 A1 | 7/2013 | Liu et al. | |
| 2014/0163338 A1 | 6/2014 | Roesicke | |

FOREIGN PATENT DOCUMENTS

| | | |
|---|---|---|
| JP | 2004208888 A | 7/2004 |
| JP | 2013-121521 A | 6/2013 |
| JP | 2016-005585 A | 1/2016 |
| WO | 2002058537 A2 | 8/2002 |
| WO | 2011025549 A1 | 3/2011 |
| WO | 2013107757 A1 | 7/2013 |

OTHER PUBLICATIONS

Chinese Patent Application 201780016577.3 Search Report. 3 pages.
Kingo Ariyoshi, Operation theory of measuring apparatus: Potentiostat used mainly in electrochemistry, Electrochemistry, Japan, Electrochemistry Society, 2012, vol. 80, No. 8, pp. 602-607, ISSN (Online): 2186-2451, DOI: 10.5796/Electrochemistry.80.602. 12 pages with translation.

* cited by examiner

ANALYTE MEASURING PATCH

FIELD OF DISCLOSURE

The present disclosure relates to the field of analyte measurement, in particular glucose measurement, in a body fluid or body tissue. It particular relates to the design of measurement and control circuitry for continuous analyte measurement.

BACKGROUND, PRIOR ART

Continuous analyte measuring systems are known for the invasive and in-vitro measurement of an analyte concentration in a patient's body fluid or tissue. They are used, for example for the continuously monitoring a diabetic's glucose level over an extended time period of a number of days up to several weeks after which they are replaced, typically directly by the patient, a relative, or the like.

The sensors that are used in such system are typically based on an amperometric measurement principle and include a number of electrodes that are arranged on a typically elongated electrode carrier. For the application, an electrode-carrying portion of the electrode carrier is placed in the patient's subcutaneous tissue and the glucose concentration is measured in the interstitial fluid. A variety of sensor and electrode designs is known in the art. The sensor electrodes and the surrounding analyte-comprising body fluid and/or tissue, in combination, form an electrochemical cell. Where not explicitly stated differently, such arrangement is also assumed in the following.

For operating such systems, sophisticated interface and measurement circuitry is required in addition to the sensor as such. In a typical design, the sensor includes three electrodes, namely a working electrode, a counter electrode and a reference electrode, and the interface and measurement circuitry is based on a circuit design generally known as potentiostat. In operation, the potentiostat applies a controlled and variable voltage to the counter electrode, thereby keeping the potential difference or voltage between the working electrode and the reference electrode at a given-constant level (polarization voltage). The current flowing between the counter electrode and the working electrode is correlated with the analyte concentrated and is measured for evaluation purposes.

While a variety of potentiostat designs is known in the art and generally available, a number of constrains and boundary conditions is present in context of the here-discussed application, which have considerable impact on the potentiostat design and the available design options, resulting in many known designs being infeasible or at least disadvantageous.

The interface and measurement circuitry is favourably arranged as close to the sensor as possible. It should accordingly be as small, compact and lightweight as possible. The electrode carrier is normally attached to an adhesive pad and projects from the adhesive pad that is placed on the patient's skin. For releasable electrical and mechanical coupling with the interface and measurement circuitry, a mechanical and electric interface structure is further provided typically directly on the patient's skin. Classical potentiostat designs, however, include a comparatively large number of complex components, such as several operational amplifiers (op-amps). It is further desirable to power sensor and circuitry with a single battery, e. g. a button cell. An asymmetric power supply, however, significantly increases the circuit complexity and number of required electronic components.

Since the involved voltages and currents at the sensor are small and directly influence the measurement results, contacting of the sensor is critical. While the sensor with the electrodes is a disposable that needs to be discarded after removal from the tissue, typical interface and measurement circuitry is too expensive to be discarded after a comparatively short application time. Costly and critical electrical connectors are accordingly required between sensor and circuitry.

It is an overall objective of the present invention to improve the state of the art regarding circuit designs of measurement circuitry for continuous analyte measurement, in particular continuous glucose measurement. Favourably, one or more of the before-mentioned drawbacks of prior art solutions is avoided fully or partly. In a general sense, the overall objective is achieved by the subject of the independent claim. Exemplary and particularly favourable embodiments are further defined by the dependent claims and the overall disclosure of the present document.

SUMMARY OF DISCLOSURE

In an aspect, the overall objective is achieved by an analyte measuring patch for invasive measuring a concentration of an analyte. The analyte measuring patch may include a sensor for transcutaneous placement in a patient's tissue, the sensor including a working electrode, a counter electrode and a reference electrode. The analyte measuring patch may further include a pad for placement on the patient's skin, wherein the sensor projects from an adhesive surface of the pad. The analyte may especially be glucose, but may also be an analyte that is present in a body fluid of a patient's body. The body fluid in which the analyte concentration shall be measured may, for example, be blood or interstitial fluid, the latter being particularly favourably for the case of glucose concentration measurement.

The working electrode, the counter electrode and the reference electrode are distinct from each other and are separately operatively coupled to the electronics unit, typically via galvanic coupling. The electrodes are arranged on a rigid, semi-rigid or soft electrode carrier which projects from the adhesive surface of the pad substantially perpendicular or alternatively in a different angle for angular placement in the tissue. Typically, the electrode carrier is realized as elongated piece of substrate. In case of the sensor being semi-rigid or soft (not sufficiently stiff or rigid to allowing direct tissue insertion), a rigid auxiliary insertion element, e. g. in form of a cannula inside which the sensor is placed for the insertion, may be present. After successful insertion, the auxiliary insertion element is retracted out of the tissue. An insertion device may be present in order to ensure a guided an optionally automated, e. g. spring-driven, insertion process. Optionally, such inserter may be designed for e. g. automated retraction of the auxiliary insertion element. The design of suited sensors an insertion devices is generally known in the art.

The analyte measuring patch may further include an electronics unit, wherein the electronics unit includes a microcontroller and a current measurement unit. The microcontroller includes a control output, a first analogue input and a second analogue input. The control output is operatively coupled with a control electrode, the control electrode being either of the working electrode or the counter electrode. The first analogue input is operatively coupled with a measurement electrode via the current measurement unit, the measurement electrode being either of the working electrode or the counter electrode. The second analogue input is operatively coupled with the reference electrode. The microcontroller is configured to control, by providing a control voltage to the control output, a potential difference between the working electrode and the counter electrode to equal a pre-defined polarization voltage.

The analyte concentration is determined by the electronics unit, typically by the microcontroller, by amperometric measurement of the current through the measurement electrode, using the current measurement unit.

In accordance with the present disclosure, the microcontroller serves, together with potential peripheral electronics, as digital potentiostat that controls a potential of the control electrode such that the potential difference between the working electrode and the reference electrode is kept substantially constant. For this purpose, the microcontroller firmware is programmed to implement a digital closed loop controller. The pre-set polarization voltage as potential difference between the working electrode and the reference electrode defines the set point of the control loop. It may be in a typical range of, e. g. 100 Millivolt to 500 Millivolt, exemplarily 350 Millivolt. The actual potential difference between the working electrode and the reference electrode defines the actual value of the control loop. It is determined from the voltages provided to the first analogue input respectively second analogue input. For this purpose, the microcontroller includes a first respectively second analogue-to-digital converter (ADC) that is associated with the first respectively second analogue input. Alternatively, a single ADC may be present that alternatively processes the voltages of the first respectively second analogue input, e. g. via multiplexing. The resolution of the ADCs may, e. g. be 12 Bit. The difference between the actual potential difference (voltage between working electrode and reference electrode) and the pre-defined polarization voltage defines the control deviation of the control loop.

Favourably, a reference voltage supply is present as part of the microcontroller or as separate part of the electronics unit, with the reference voltage being maintained constant for a varying supply voltage. Via this constant reference voltage and the closed loop controller, the polarization voltage between the reference electrode and the working electrode is maintained constant under varying conditions.

For the proposed design, a majority of structurally distinct and separate electronics components that is typically required for realizing a potentiostat can be omitted and only a small number of components is required in addition to the microcontroller. The microcontroller may be a commercially available state-of-the-art microcontroller that typically includes a number of analogue inputs as well as further input/output interfaces.

For an arrangement in accordance with the present disclosure, the polarization voltage may be positive or negative in dependence of the sensor design. Furthermore, current flow may be from the working electrode to the counter electrode or vice versa. Furthermore, either of the working electrode and the counter electrode may serve as control electrode and either of the working electrode and the counter electrode may serve as measurement electrode. A number of these variants will be discussed in more detail in the context of exemplary embodiments.

In some embodiments, the input voltage range that may be converted by the ADCs at the analogue inputs as well as the output voltage range at the analogue output depend on the supply voltage of the electronics unit. In an embodiment that is assumed in the following, the minimum voltage that may be converted equals or substantially equals zero (measured against ground), and the maximum voltage that may be converted substantially corresponds to the (positive) supply voltage, i. e. the voltage span substantially equals the supply voltage.

In some favourably embodiments that are also assumed in the following, the microcontroller further includes an internal voltage reference, in particular a voltage reference for the analogue-to-digital conversion that provides a substantially constant absolute reference voltage over a large range of the battery supply voltage. In this way, the polarization voltage may be maintained at a constant absolute value even though the battery supply voltage varies. A voltage reference external to the microcontroller, however, may optionally be used.

In an embodiment, the electronics unit includes a voltage follower and the reference electrode is operatively coupled to the second analogue input via the voltage follower. The voltage follower may be realized based on an operation amplifier (op-amp) as generally known in the art. For accurate measurement results and in order to avoid potential sensor damage that may result from a current flow through the reference electrode, it is of major importance that the potential of reference electrode is measured in a static way, i. e. with the current flow through the reference electrode being negligible. Consequently, a current flow is present only between the working electrode and the counter electrode. In particular embodiments, the op-amp of the voltage follower is the only electronic component between the reference electrode and the second analogue input and the output of the voltage follower op-amp is directly galvanic coupled to the second analogue input and the reference electrode is favourably directly galvanic coupled to the non-inverting input of the voltage-follower op-amp. Within the context of this document, "direct galvanic coupling" means a coupling without electronic components in the flow path, but does not necessarily exclude the presence of electrical contacts or connectors.

In an embodiment, the microcontroller includes a digital-to-analogue converter in operatively coupling with the control output, and the control electrode is operatively coupled to the control output via direct galvanic coupling or via a sample-and-hold unit, the sample-and-hold-unit preferably being a passive RC network. The control output may output the voltage continuously, in which case the control electrode is favourably directly galvanic coupled. For energy saving reasons, the control output may provide the control voltage only intermittently respectively periodically with a comparatively low duty cycle. In some embodiments, the duty cycle may be as lows as 5% to 10%. The absolute frequency may be selected in a wide range from, e. g. 10 Hz up to several hundred kHz. A favourably passive "sample-and-hold" unit respectively low pass filter may be provided to continuously provide the control voltage to the control electrode with sufficient stability. Such "sample-and-hold" unit respectively low pass filter may be realized by an RC network as generally known in the art, e. g. with a single resistor and a single capacitor.

While one or more DACs are included in many state-of-the art microcontrollers, this is not necessarily the case. Alternatively to directly generating the control voltage via a DAC, the control output may be a digital binary output at which the microcontroller outputs a binary control signal with Pulse Width Modulation (PWM). In this case, a passive low pass filter RC network may be provided to generate the control voltage from the pulse width modulated signal.

In an embodiment, the current measurement unit includes a differential amplifier unit or a current-to-voltage converter unit.

Both differential amplifiers and voltage converters may be based on an op-amp and additional passive components, in particular resistors, as known in the art. The circuitry may further comprise additional components and/or functional units, in particular inverting and/or non-inverting amplifiers, which are favourably also realised based on op-amps.

Exemplary and particularly favourably specific circuit designs are discussed further below in the context of exemplary embodiments.

In an embodiment, the control electrode is different from the measurement electrode. Alternatively, however, the control electrode and the working electrode may be identical.

In an embodiment, the control electrode is the counter electrode and the measurement electrode is the working electrode. In an alternative embodiment with the working electrode being different from the measurement electrode, the control electrode is the working electrode and the measurement electrode is the counter electrode.

In an embodiment, the electronics unit is operatively coupled to or designed for operatively coupling to an asymmetric power supply, in particular a single-voltage power supply. An asymmetric power supply is favourable because it can be realized with a single battery of, e. g. the button cell type. An analyte measuring patch in accordance with the present invention can be favourably realized with an asymmetric power supply, without requiring a significant amount of additional circuitry or components.

In some embodiments, the potential of one of the working electrode or the counter electrode is fixed to a reference potential, e. g. ground, by direct galvanic coupling.

In some embodiments, the potential of one of the electrodes, in particular the counter electrode, is shifted via corresponding circuitry for offset compensation purposes and/or to allow the measurement of a current between the working electrode and the counter electrode that is opposite to the standard current direction according to the sensor and circuitry design. Such potential shifting may be realized via a potential shifting unit which may be realized via a passive RC network, a shifting voltage that is generated via a DAC, a PWM signal with associated filtering/smoothing circuitry, an additional voltage reference or voltage regulator, or the like.

In an embodiment, the microcontroller is configured to detect air bubbles in contact with at least one of the working electrode, the counter electrode and/or the reference electrode.

Air bubbles may be detected via corresponding algorithms that may be implemented by the microcontroller. The presence of air bubbles is reflected by considerable signal distortions. Air bubbles contacting or surrounding one or more of the electrode result in the analyte concentration measurement being inaccurate, and potentially the analyte concentration measurement being impossible.

Similarly, the microcontroller may be configured, via implementing corresponding algorithms, to detect further errors, defects, and/or hazardous situations, such as defective components or broken sensor connections. For this purpose, the controller may, e. g., be configured to temporarily vary the control voltage and/or polarization voltage according to a test schedule, e. g. once a day and for a short time period, and detect whether the signals as received from the sensor via the analogue inputs reflect such variation as expected.

In some embodiments, the microcontroller may further be configured to execute further routines associated with the analyte concentration measurement, such as a separation of AC and DC components of the measurement signal, and/or signal conditioning like smoothing, distortion/artefact removal, calibration, linearization, and the like. Such routines or algorithms may include digital signal processing and filtering algorithms as generally known in the art, including adaptive filters, such as Kalman filters.

Some or all of the before-described functionality, such as hazard/error detection and signal processing may alternatively or additionally be implemented on further units or devices of an analyte measurement system, as discussed further below in more detail.

In an embodiment, the electronics unit and the sensor are non-detachably mechanically coupled. In such an embodiment, the sensor, the pad and the electronics components of the patch form a structurally compact and integral unit that is used for a certain application time and subsequently discarded as a whole. The circuitry is favourably arranged in a corresponding enclosure or housing and arranged on the non-adhesive surface of the pad, opposite to the sensor. Such enclosure or housing may further include a power supply, e. g. a button cell battery, and further components as discussed further below in the context of various system architectures. Favourably, the galvanic coupling between electrodes and circuitry is hard wired, thus avoiding releasable electric connectors.

In an embodiment, the sensor and the electronics unit are detachably mechanically coupled or designed to detachably mechanically couple. For this type of embodiment, releasable or detachable contacts are provided for the electric coupling of sensor electrodes and the electronics unit. Corresponding electrical and mechanical interface structures may be provided on the non-adhesive surface of the pad and an enclosure or housing of the electronics unit, thus providing a releasable or detachable coupling e. g. via snap-fit. For this type of embodiment, the pad and the sensor form a common disposable sensor and pad unit of comparatively short application time, while the application time of the electronics unit, favourably including the power supply, may be significantly longer, e. g. in the range of a year or more and may be used with a plurality of sensor and pad units in sequence.

Some favourable examples for the overall system architecture of an analyte measuring patch are described in more detail further below in the context of exemplary embodiments.

In an embodiment, the electronics unit includes a data communication unit, the electronics unit being designed to exchange, via the data communication unit, data, in particular analyte concentration data or data correlated with analyte concentration, with a further electronics unit.

The data that are communicated may be processed analyte concentration data. This is the case in embodiments where the electronics unit, namely the microcontroller, implements the data processing algorithms and routines for computing an analyte concentration, such as routines and algorithms, for linearization calibration, filtering, etc. Alternatively, the data that are transmitted may be pre-processed measurement data or raw data.

In an embodiment, the data communication unit is a wireless data communication unit, preferably a near field communication unit. Favourably, the electronics unit is environmentally sealed. The near filed communication unit may be an RFID communication unit as commercially available or may another type of wireless data communication unit, such as an application specific inductive and/or capacitive communication unit. The environmentally sealing favourably provides a sealing and protection that allows the electronics unit to be used in typical everyday situation, including, e. g. showering or bathing.

In an embodiment, the analyte measuring patch further includes a further electronics unit, the further electronics unit including a further data communication unit for operatively coupling with the data communication unit, the further electronics unit being designed to detachably mechanically couple to the electronics unit.

In such an embodiment, the electronics unit of the analyte measuring patch mainly includes the circuitry that is directly associated with the measurement. The further electronics unit may include one or more further microcontrollers, microprocessors, data storage, high-level signal evaluation and/or signal analysis unit, or the like.

In an embodiment of the analyte measuring patch the electronics unit and the further electronics unit each include separate power supplies.

In an embodiment, the analyte measuring patch further includes a wireless remote device communication unit, the wireless remote device communication unit being operatively coupled to the microcontroller and being designed to exchange data, in particular analyte concentration data or data correlated with analyte concentration, with a further separate remote device.

In a further aspect, the overall objective is achieved by a method for measuring a concentration of an analyte, in particular glucose, and/or a method for operating an analyte measuring patch. The method includes providing an analyte measuring patch. The analyte measuring patch includes a sensor for transcutaneous placement in a patient's tissue. The sensor includes a working electrode, a counter electrode and a reference electrode, and a pad for placement on the patient's skin, wherein the sensor projects from an adhesive surface of the pad. The analyte measuring patch further includes an electronics unit, wherein the electronics unit includes a microcontroller and a current measurement unit.

The method may include operatively coupling a control output of the microcontroller with a control electrode, the control electrode being either of the working electrode or the counter electrode. The method may further include operatively coupling a first analogue input of the microcontroller with a measurement electrode via the current measurement unit, the measurement electrode being either of the working electrode or the counter electrode. The method may further include operatively coupling a second analogue input of the microcontroller with the reference electrode. Alternatively, the working electrode, the counter electrode and the reference electrode may be operatively coupled as part of the analyte measuring patch prior to carrying out the method. The method may further include controlling, by providing a control voltage to the control output, a potential difference between the working electrode and the counter electrode to equal a pre-defined polarization voltage.

An analyte measuring patch in accordance with the present disclosure may be used for carrying out a method in accordance with the present disclosure. Therefore, particular embodiments of an analyte measuring patch disclose, at the same time, corresponding embodiments of a method for measuring the concentration of an analyte, and vice versa.

EXEMPLARY EMBODIMENTS

Figure 1:
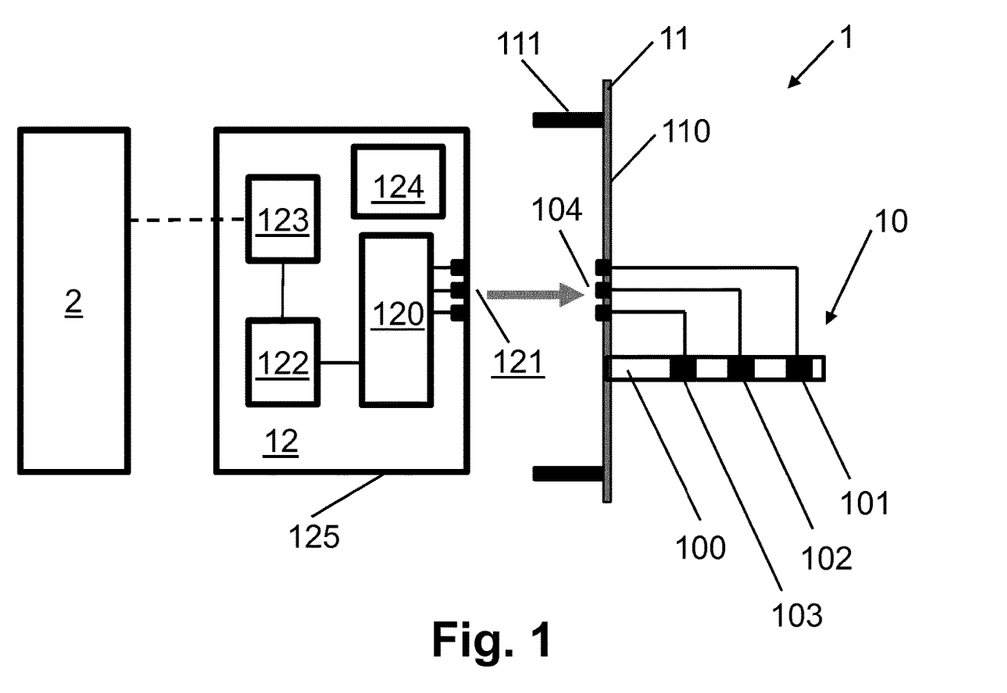
FIG. 1 shows an exemplary embodiment of an analyte measuring patch.

In the following, reference is first made to FIG. 1. FIG. 1 shows an exemplary embodiment analyte measuring patch 1 in accordance with the present disclosure in a schematic combined structural/functional view. Like in following further figures, the specific arrangement and relative locations of the individual elements do not imply any particular design and/or geometric arrangement, unless explicitly stated differently. By way of example, the analyte is glucose and the analyte measuring patch 1 is designed for measuring glucose concentration inside the interstitial tissue.

The analyte measuring patch 1 includes a sensor 10, a pad 11, and an electronics unit 12.

The sensor 10 includes an electrode carrier 100 that is designed for transcutaneous placement in a patient's tissue, either manually or using an insertion device. In its subcutaneous portion, i. e. its portion that is arranged under the skin during application, the electrode carrier 100 carries three electrodes, namely a working electrode 101, a reference electrode 102, and a counter electrode 103, the three electrodes being distinct from each other. Suited sensor designs that may be used in the context of analyte measuring patch 1 are known in the art.

The pad 11 comprises an adhesive surface 110 that is designed to be attached to the patient's skin, with the sensor 10 respectively the electrode carrier 100 projecting from the adhesive surface 110 perpendicularly (as exemplarily shown) or in another desired angle. The three electrodes 101, 102, 103 are in galvanic or wired connection with a set of corresponding set 104 of sensor contacts, that are arranged on a (typically non-adhesive) side of the pad 11 pointing away from the skin. A mechanical interface structure 111 is provided on the patch for releasable mechanical coupling with an electronics unit as described in the following and may include snap-fitting elements, catches, latches, or the like as generally known in the art. In the shown embodiment, the sensor 10, the pad 11 and their associated components form a non-separable disposable unit that is designed to be used for a limited time of a number of days of up to a number of weeks and to be subsequently discarded.

The electronics unit 12 includes a microcontroller-based digital potentiostat unit 120, a set 121 of electronics unit contacts, a supplementary electronics unit 122, a remote device communication unit 123, and a power supply in form of a single battery 124, e. g. a button cell.

The before mentioned components of the electronics unit 12 are enclosed by a housing 12. The housing 12 is designed for releasable engaging with the mechanical interface structure 111 on the pad. The contacts of the set 121 of electronics unit contacts are accessible from outside the housing and arranged such that they connect to the corresponding contacts of the set 104 of sensor contacts upon engagement of the housing 125 and the mechanical interface structure 111, thus providing a galvanic coupling of the electrodes 101, 102, 103 and the digital potentiostat unit 120. In some embodiments, the housing 125 is hermetically and environmentally sealed, in particular watertight, and is not designed to be opened. In such embodiments, the battery 124 may be designed to provide power for the whole lifetime of, e.g. 6 or 12 months of the electronics unit 12, or may be rechargeable and be charged, e. g. via inductive coupling of additional charging contacts (not shown). Alternatively, the battery 124 may be exchangeable. The electronics unit 12 is designed to be used in in combination with a plurality of disposable units in sequence.

The supplementary electronics unit 122 provides functionality that is required in addition to the digital potentiostat unit 120 and is operatively coupled with the digital potentiostat unit 120. It may provide functionality such as linearization, filtering, calibration, data storage, etc., as described above.

Via the remote device communication unit 123, the electronics unit 12 may operatively couple to and exchange data with a further remote device 2 e. g. according to the Bluetooth standard or any other suited general purpose or proprietary communication standard and/or protocol. The further remote device 2 may, e. g. be a diabetes management device of similar design and shape as a cell phone. The remote device 2 is typically used to show measured analyte values, analyte-versus-time graphs, statistic evaluations etc. The remote device 2 may further be designed for storing measured analyte concentrations, and may further be designed for coupling with still further devices, such as a Personal Computer (PC). The remote device may further be used for transmitting data, in particular calibration data, to the electronics unit.

In some embodiments, the electronics unit 1 and the remote device 2 are designed to operatively couple substantially continuously, with measured analyte concentration data being continuously transmitted to the remote device 2. Alternatively, the electronics unit may be designed to store the measured analyte concentration data internally, e. g. in the supplementary electronics unit, and transmit them from time to time according to a fixed schedule, or on demand, with the transmission being, e. g. initiated by a user on the remote device. In a further variant, only a single analyte concentration value, e. g. blood glucose value, is determined and transmitted to the remote device 2 on demand.

Alternatively to a diabetes management device the remote device 2 may be a drug delivery device, in particular an insulin pump. In such embodiment, analyte concentration data that are measured by the patch 1 are used for controlling drug administration by the drug delivery device, e. g. according to a closed loop or semi closed loop as generally known in the art. In a further embodiment, the electronics unit 12 is designed to couple, via its remote device communication unit 123, to a number of remote devices.

It is noted that the separation between the single functional units of the electronics unit 12, in particular the separation between the digital potentiostat unit 120 and the supplementary electronics unit 122, is for clarity reasons only and does not imply a particular technical implementation. Typically, the functionality of the supplementary electronics unit 122 is realized, fully or partly, by the same microcontroller as used in the digital potentiostat unit 120 and corresponding firmware. The supplementary electronics unit 122 and the digital potentiostat unit may accordingly also be considered as common unit.

Figure 2:
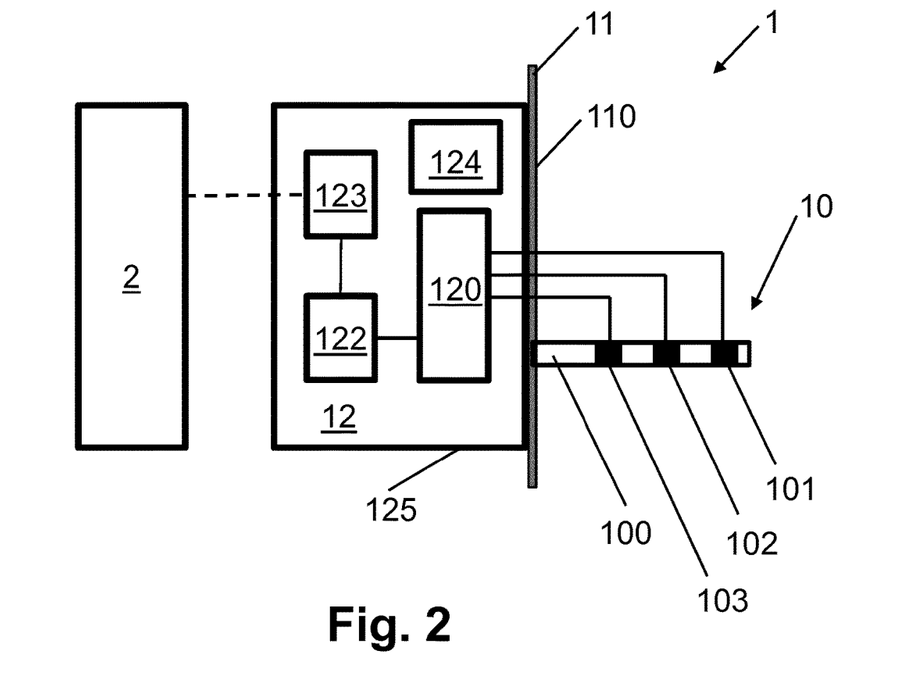
FIG. 2 shows a still further exemplary embodiment of an analyte measuring patch.

In the following, reference is additionally made to FIG. 2. FIG. 2 shows a further exemplary embodiment analyte measuring patch 1 in accordance with the present disclosure in a schematic combined structural/functional view, similar to FIG. 1. Since the embodiment of FIG. 2 corresponds to the embodiment of FIG. 1 in a number of aspects, only deviating or differentiating features are discussed in the following.

In the embodiment of FIG. 2, the mechanical interface structure 111, the set 104 of sensor contacts, 104, and set of electronics unit contacts, 121, are omitted. Instead, the electronics unit 12 respectively the electronic unit housing 125 is non-detachably attached to the pad 11, e. g. via gluing or ultrasonic welding. The housing 125 favourably encloses and capsules the components of the electronics unit 12 in an environmentally tight and in particular watertight way.

The embodiment of FIG. 2 has a number of advantages both from a technical and a handling or application point of view. As explained before, omitting lack of releasable electrical contacts between the electrodes 101, 102, 103 and the digital potentiostat circuit is technically favourable in view of the comparatively low potentials respectively voltages and currents involved. Furthermore, environmentally sealing is easier. While the embodiment of FIG. 1 sealing means are favourably provided in the area of the sets of contacts, 104, 121, no such means are required in the embodiment of FIG. 2. Due to the lack of releasable couplings and the accordingly reduced number of handling steps, everyday application is particularly simple. This aspect is of particular relevance for diabetic patients who are often visually and/or tactilely impaired.

A drawback of the embodiment of FIG. 2 is the need to discard the whole analyte measuring patch 1 at the end of its comparatively short lifetime, including in principle reusable electronics components and battery. Long term application costs are accordingly critical. Thanks to the comparatively low number of costs of the required electronic components for the design of an electronics unit, namely a digital potentiostat in accordance with the present disclosure, it is feasible from an economic point of view.

Figure 3:
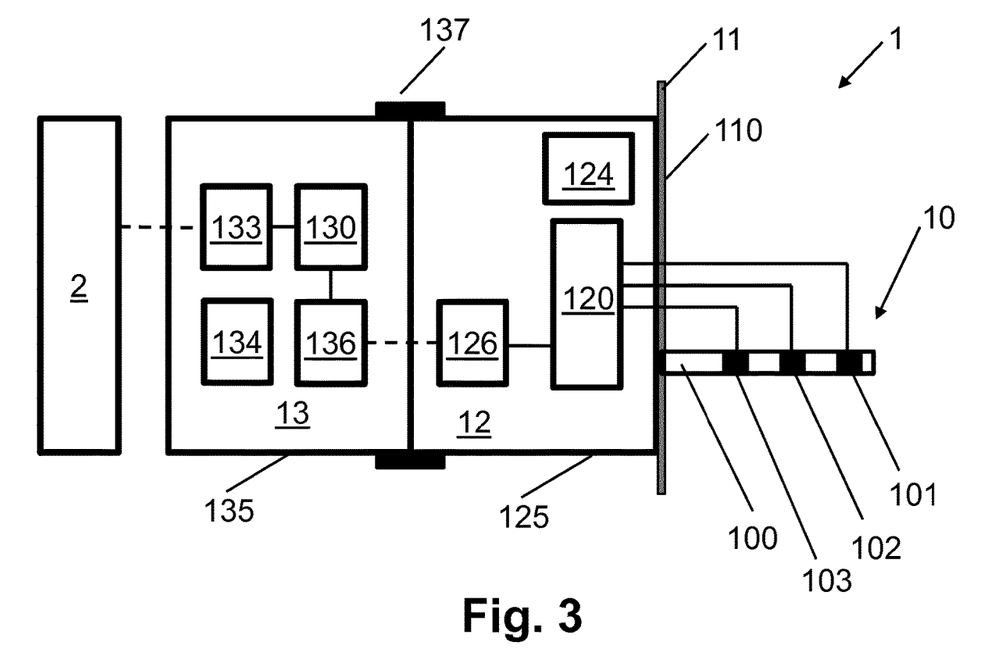
FIG. 3 shows a still further an exemplary embodiment of an analyte measuring patch.

In the following, reference is additionally made to FIG. 3. FIG. 3 shows a further embodiment of the analyte measuring patch 1. In this embodiment, the electronics unit is designed in a generally similar way as the embodiment of FIG. 2, with the sensor 10, the pad 11 and the electronics unit 12 favourably forming a common and on-detachable unit and in particular a unit direct galvanic coupling between electrodes 101, 102, 103 and digital potentiostat circuit 120.

In contrast to the embodiment of FIG. 2, however, the electronics unit 12 comprises a data communication unit 126, in particular a Near Field Communication (NFC) unit such as an RFID unit.

A further electronics unit 13 with a further electronics unit housing 135 is present. The electronics unit 12 and the further electronics unit 13 are designed for reliably coupling via a coupling structure 137. Favourably, the further electronics unit housing 135 environmentally seals the further electronics unit 13.

The further electronics unit 13 includes a further data communication unit 136 that is designed to exchange and in particular receive data from the data communication unit 126. The further electronics unit 13 further includes an electronics module 130 in operative coupling with the further data communication unit 136 and essentially takes over the functionality of the supplementary electronics unit 122 in the alternative embodiments of FIG. 1 and FIG. 2. The electronics module 130 is operatively coupled with a wireless remote device communication unit 133 for data exchange with a remote device 2 as discussed above. The further electronics unit 13 is powered via further electronics unit power supply 134, e. g. a battery. In contrast to the electronics unit 12, the further electronics unit 13 is reusable and designed to be uses for an extended lifetime.

The embodiment of FIG. 3 shows the same advantage as the embodiment of FIG. 2 that no releasable contacts are required for connecting the sensor 10 and that the electronics unit housing 125 can be favourably designed to be environmentally sealed. In addition, the battery 124 may be smaller since as compared to the embodiment of FIG. 2 since it powers less components and only near-filed data communication is required. In addition, fewer electronics components are present in the disposable electronics unit 12. In particular, comparatively expensive components, such as the remote device communication unit 133 (e. g. a Bluetooth module as explained before) are non-disposable.

In a variant, the supplementary electronics unit 122 is still present in the electronics unit and carries out tasks such as filtering, calibration and/or linearization, while the electronics module 130 is used for high-level data evaluation, data storage etc. In a further variant, the electronics unit.

In a further variant, the power supply or battery 124 of the electronics unit 12 is omitted and the electronics unit 12 is supplied from the further electronics unit e. g. via inductive coupling.

Independent of the specific type of embodiment, alarming device, e. g. an acoustic alarming device in form of an acoustic transducer and/or an tactile alarming device in form of a pager vibrator, may optionally be present in order to provide an alarm to the user e. g. in case of a device fault or a critical situation regarding the measured analyte concentration, e. g. a situation of hypoglycemia or hyperglycemia in case of the analyte being glucose. For the embodiment of FIG. 1, or FIG. 2, an alarming device may be part of the disposable electronics unit, e. g. the supplementary electronics unit 122. In the embodiment of FIG. 13, an alarming device may favorably be part of the further electronics unit 13, e. g. part of the electronics module 130.

Figure 4:
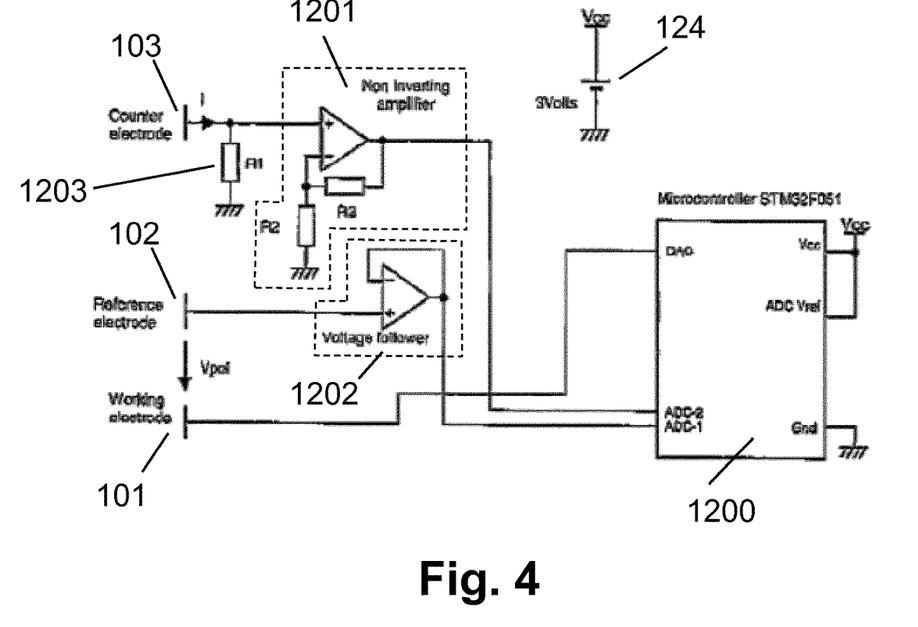
FIG. 4 shows an exemplary embodiment of a measurement and control circuit.

In the following, reference is additionally made to FIG. 4. FIG. 4 shows a circuit diagram of an exemplary measurement and control circuit or digital potentiostat circuit 120 in accordance with the present disclosure. The digital potentiostat circuit 120 includes a microcontroller 1200, a non-inverting amplifier 1201, a voltage follower 1202, and a current-to-voltage converter 1203. As explained before, the microcontroller may additionally be configured or programmed to carry out further tasks. It is noted that the indicated type of microcontroller is exemplary and may be replaced by a variety of other microcontrollers.

In FIG. 4 and further exemplary embodiments, as well as in the description, the following convention is used. The polarization voltage Vpol is considered to be positive if the potential of the reference electrode is lower than the potential of the working electrode. The current between the working electrode and the counter electrode is considered positive if it flows from the working electrode into the counter electrode, as indicated by the corresponding voltage and current arrows in the circuit diagrams. Other conventions, however, may be used as well.

In the embodiment, the current between working electrode and counter electrode is converted into a proportional voltage by current-to-voltage converter 1203 in form of resistor R1 that is connected to the counter electrode 103. This voltage is fed into an op-amp based non-inverting amplifier 1201 and fed into a first analogue input ADC-2 of the microcontroller 1200. The counter electrode accordingly serves as measurement electrode.

The reference electrode 102 is coupled to a second analogue input ADC-1 of the microcontroller 1200 via a voltage follower 1202. The voltage follower 1202 serves as impedance converter of virtually infinite input impedance and ensures that the voltage at the second analogue input corresponds to the voltage of the reference electrode 102 (measured against ground), but there is no current flow through the reference electrode 102. The only current flow is between the working electrode 101 and the counter electrode 103.

The working electrode 101 is directly galvanic coupled to a control output DAC of a digital-to-analogue converter of the microcontroller 1200. The working electrode accordingly serves as control electrode.

The microcontroller 1200 is programmed to output a control voltage at the control output—thereby adjusting the current between working electrode 101 and the counter electrode 103—such that the voltage between the working electrode 101 and the reference electrode 102 corresponds to the preset polarization voltage. Updating and outputting the control voltage is carried out repeatedly or virtually continuously, e. g. 1 to 50 times per second.

In the circuit diagram of FIG. 4, like in further circuit diagrams as described further below, a voltage supply that is connected to connector Vref of the microcontroller 1200 provides a supply voltage for an internal voltage reference of, e. g. 1.2 V of the microcontroller 1200. The voltage of the voltage reference however, is not dependent on the precise voltage supplied to Vref which accordingly does not need to be stabilized. It may therefore be simply connected to the battery 124 and is supplied with the battery voltage Vcc. The minimum and maximum voltage that may be converted by the ADCs and DAC of the microcontroller 12000 is, as described before, defined by Vcc.

Figure 5:
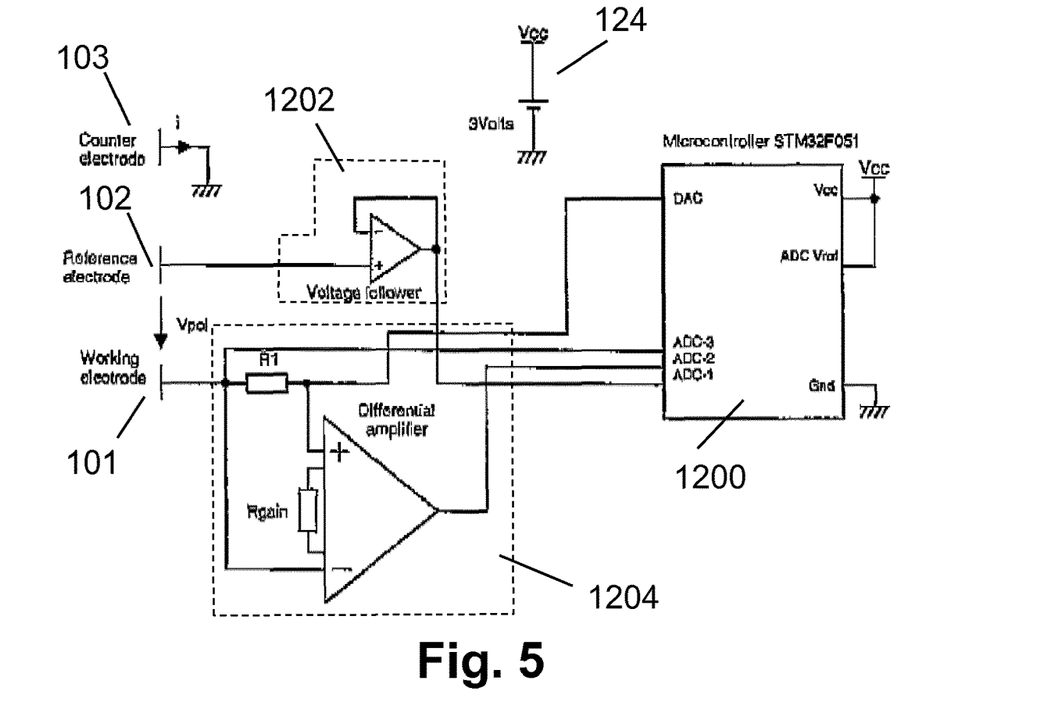
FIG. 5 shows a further exemplary embodiment of a measurement and control circuit.

In the following, reference is additionally made to FIG. 5. FIG. 5 shows a further embodiment of the digital potentiostat circuit 120. In principle, the design as shown in FIG. 5 is similar to the design as shown in FIG. 4. However, in the design of FIG. 5, the working electrode 101 serves as both measurement electrode and control electrode, while the counter electrode 103 is galvanic coupled to ground, which is advantageous with respect to stability. In this embodiment, the working electrode 101 is connected to both the negative/inverting input of an op-amp based differential amplifier 1203 and a third analogue input ADC-3 of a third analogue-to-digital converter. The positive/non-inverting input of the differential amplifier 1204 is coupled to the control output DAC, and the output of the differential amplifier 1204 is coupled to the first analogue input ADC-2. R1 is a resistor defining the input impedance (impedance between positive/non-inverting and negative/inverting input) and resistor Rgain defines the gain of differential amplifier 1204. In this embodiment, a third analogue input and a third analogue-to-digital converter are required in order to compensate the voltage drop over the input impedance R1.

Figure 6:
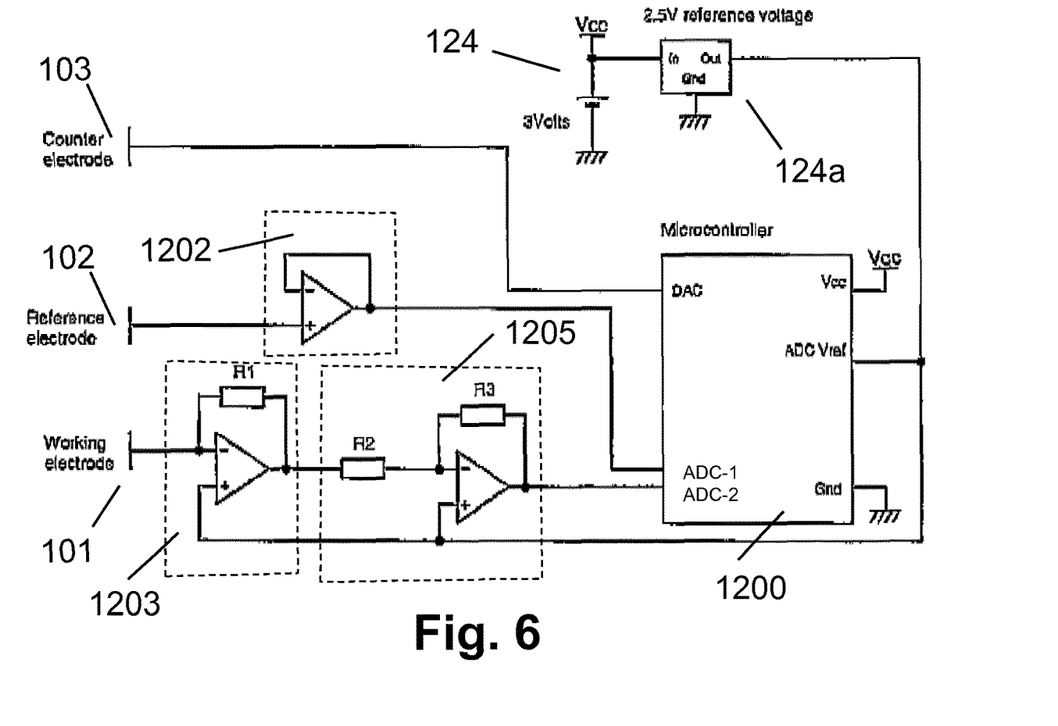
FIG. 6 shows a still further exemplary embodiment of a measurement and control circuit.

In the following, reference is additionally made to FIG. 6. FIG. 6 shows a further embodiment of the digital potentiostat circuit 120. In the embodiment, the counter electrode 103 serves as control electrode and is directly coupled to the control output DAC. The working electrode 101 serves as measurement electrode and is connected to the first analogue input ADC-2 via a series of an (inverting) current-to-voltage converter 1203 and an inverting op-amp based amplifier 1205. In this example, the current-to-voltage converter 1203 is also op-amp based.

In the embodiment of FIG. 6, a further external 2.5V reference voltage supply 124a is provided that is connected to the non-inverting inputs of the op-amps of the current-to-voltage converter 1203 and an inverting op-amp based amplifier 1205. In this example, the current-to voltage converter 1203 has an output voltage of 2.5V (reference voltage as supplied by external reference voltage supply 124) and Vcc, while the inverting amplifier 1205 provides an output voltage 0 . . . 2.5V. Further in the example, the connector Vref of the microcontroller 1200 is coupled to the external reference voltage supply 124a, which, however, is not essential.

Figure 7:
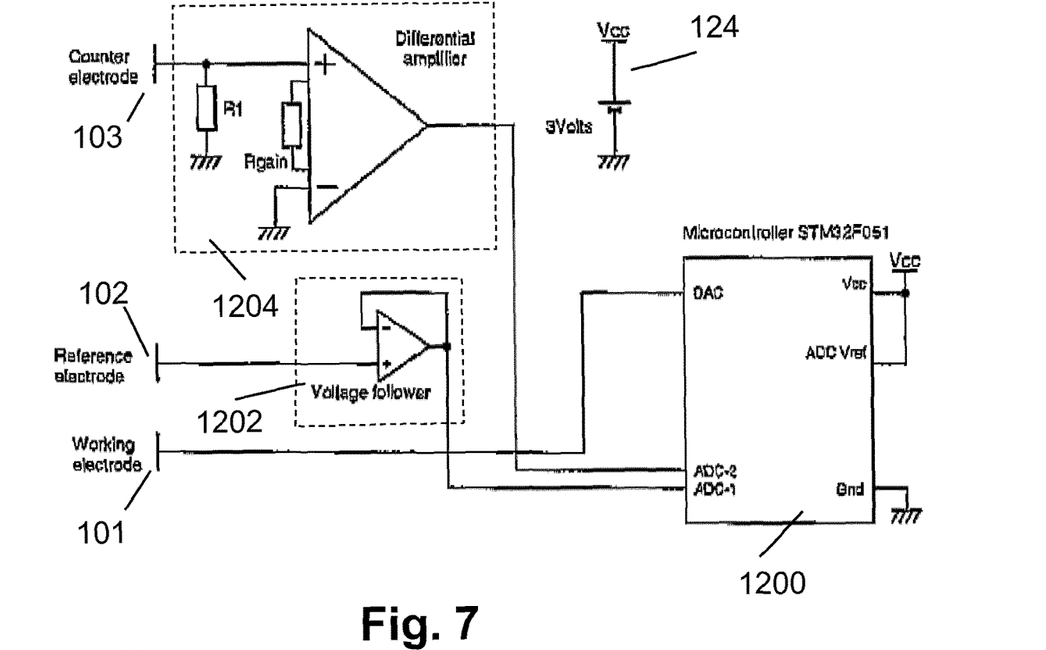
FIG. 7 shows a still further exemplary embodiment of a measurement and control circuit.

In the following, reference is additionally made to FIG. 7. FIG. 7 shows a further embodiment of the digital potentiostat circuit 120. Like in the embodiment of FIG. 4, the working electrode 101 serves as control electrode, while the counter electrode 103 serves as measurement electrode. In contrast to the embodiment of FIG. 4, however, the counter electrode 103/measurement electrode is coupled to the first analogue input ADC-2 via differential amplifier 1204.

Figure 8:
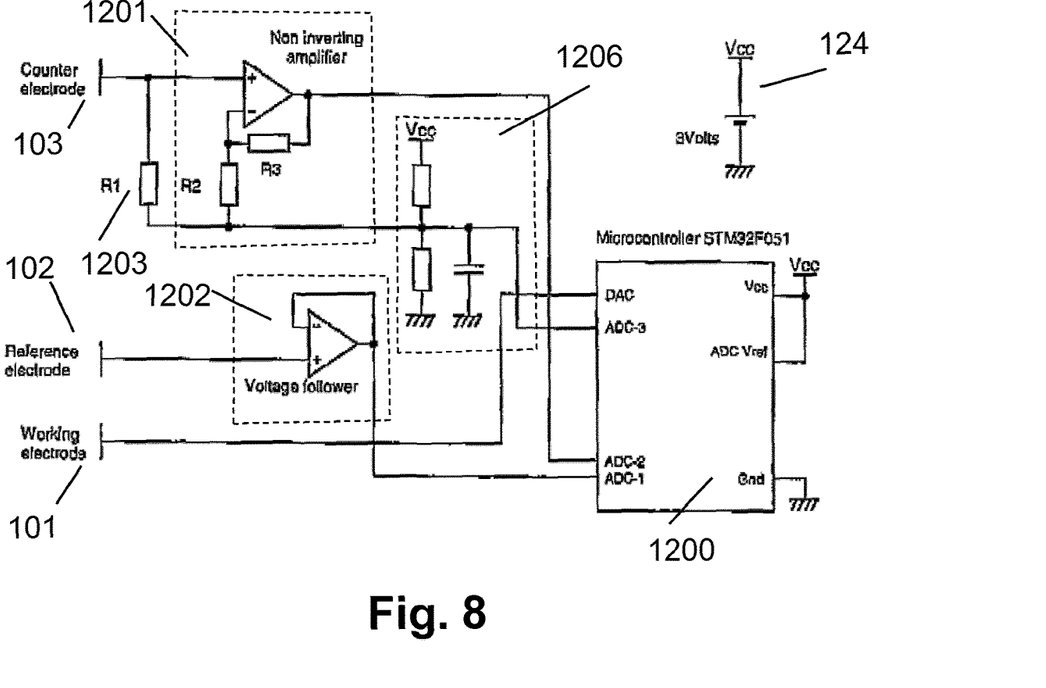
FIG. 8 shows a still further exemplary embodiment of a measurement and control circuit.

In the following, reference is additionally made to FIG. 8. FIG. 8 shows a further embodiment of the digital potentiostat circuit 120. In most aspects, the embodiment of FIG. 8 is similar to the embodiment of FIG. 7. However, an additional RC-network 1206 is present in this embodiment which serves as potential shifting unit and shifts the potential of the counter electrode 103. Shifting the counter electrode potential may be favorable to allow the detection of negative current and/or compensate the offset of the op-amp in non-inverting amplifier 1201. A third analogue input ADC-3 of the microcontroller 1200 is used in this embodiment to measure the potential shift.

Figure 9:
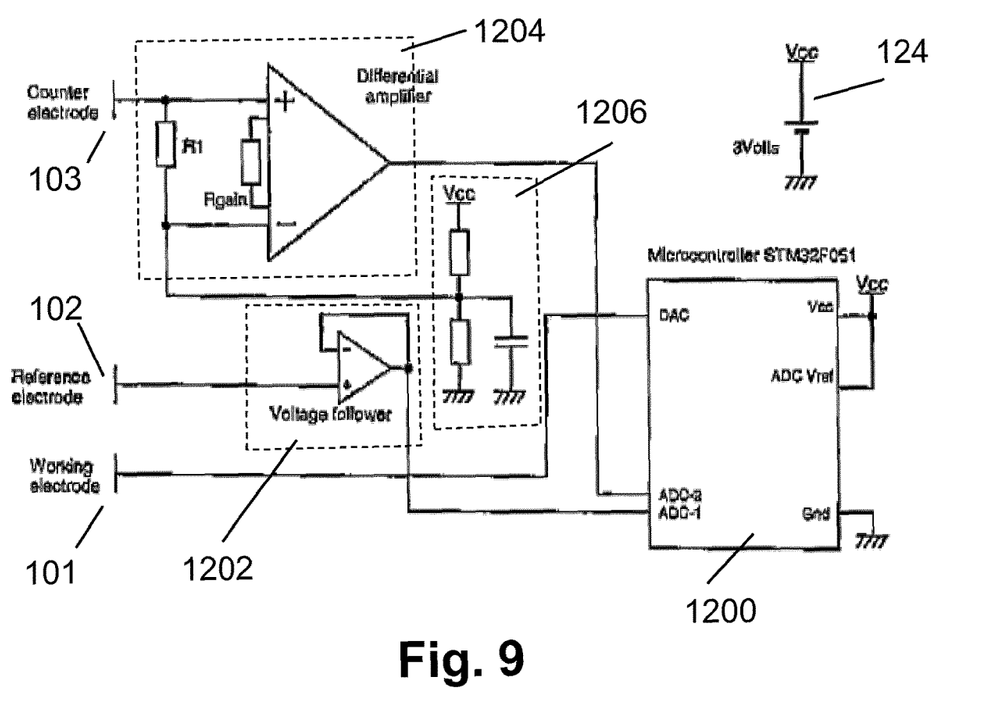
FIG. 9 shows a still further exemplary embodiment of a measurement and control circuit.

In the following, reference is additionally made to FIG. 9. FIG. 9 shows a further embodiment of the digital potentiostat circuit 120. In most aspects, the embodiment of FIG. 9 is similar to the embodiment of FIG. 8. However, the counter electrode 103 is coupled to the first analogue input ADC-2 via a differential amplifier 1204 rather than non-inverting amplifier 1201. The counter electrode 103 is coupled to the positive/non-inverting input and the shift voltage as determined by RC-network 1206 is fed into the negative-inverting input of differential amplifier 1204. In contrast to the embodiment of FIG. 8, the embodiment of FIG. 9 does not require the third analogue input.

Figure 10:
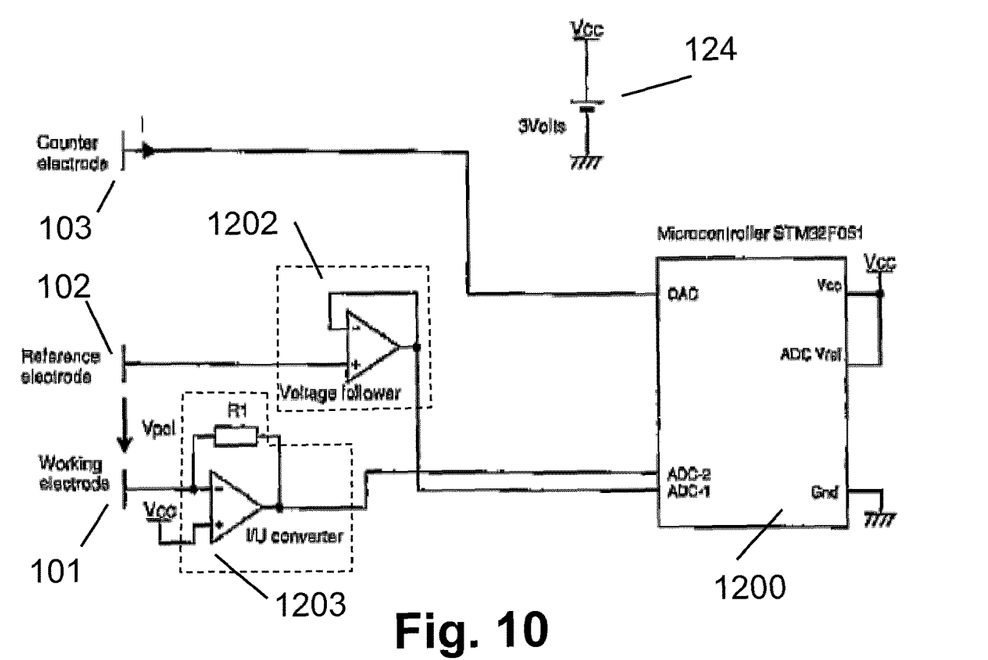
FIG. 10 shows a still further exemplary embodiment of a measurement and control circuit.

In the following, reference is additionally made to FIG. 10. FIG. 10 shows a further embodiment of the digital potentiostat circuit 120. The embodiment of FIG. 10 is designed for a positive polarization voltage and negative current between working electrode 101 and counter electrode 103 and requires a particularly small number of components for this configuration. In the embodiment of FIG. 10, the counter electrode 103 is coupled to the analogue output DAC and accordingly serves as control electrode. The working electrode 101 serves as measurement electrode and is coupled to the first analogue input ADC-2 via op-amp based current-to-voltage converter 1203, with the positive/non-inverting input of the op-amp being coupled to the supply voltage. Alternatively to voltage-to current converter 1203, a differential amplifier could be used for the current measurement. In further variants, the working electrode 101 serves as control electrode and current measurement is performed at the counter electrode 103 and either of the working electrode 101 or the counter electrode 103 serve serves as measurement electrode.

Figure 11:
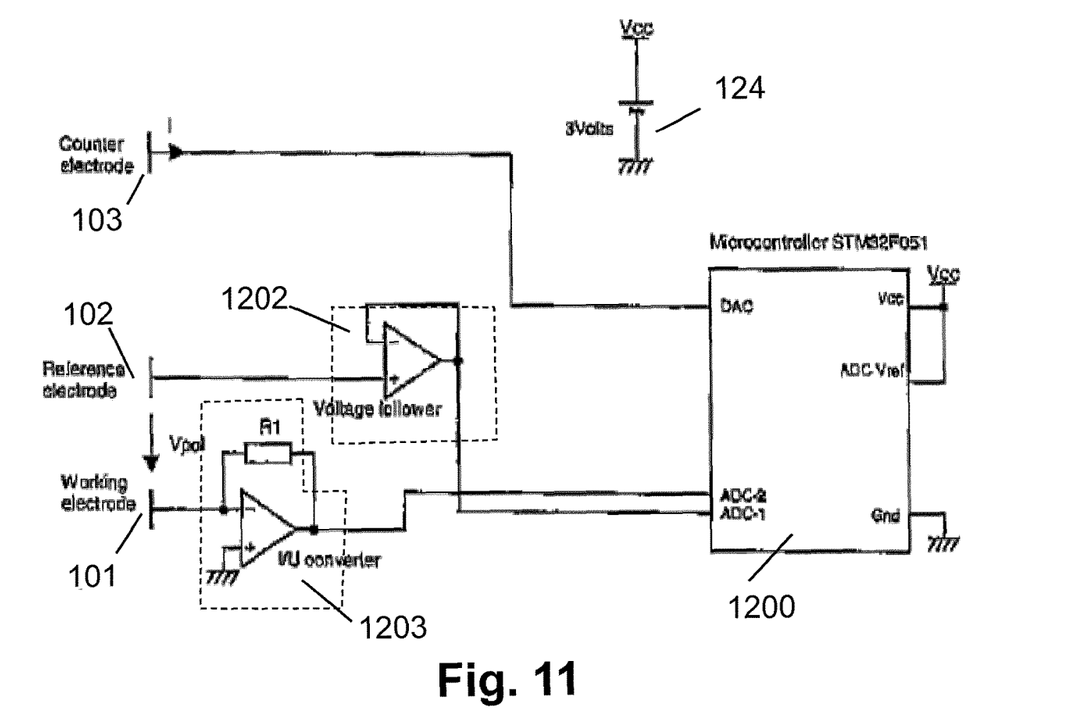
FIG. 11 shows a still further exemplary embodiment of a measurement and control circuit.

In the following, reference is additionally made to FIG. 11. FIG. 11 shows a further embodiment of the digital potentiostat circuit 120. The embodiment of FIG. 11 is designed for a negative polarization voltage and positive current between working electrode 101 and counter electrode 103 and requires a particularly small number of components for this configuration. The embodiment of FIG. 11 is similar to the embodiment of FIG. 10. As sole difference, the positive/non-inverting input of the op-amp is coupled to ground rather than to the supply voltage.

In a variant, the working electrode 101 serves as control electrode and the current is measured via a voltage-to-current converter at the counter electrode which accordingly serves as measurement electrode.

Figure 12:
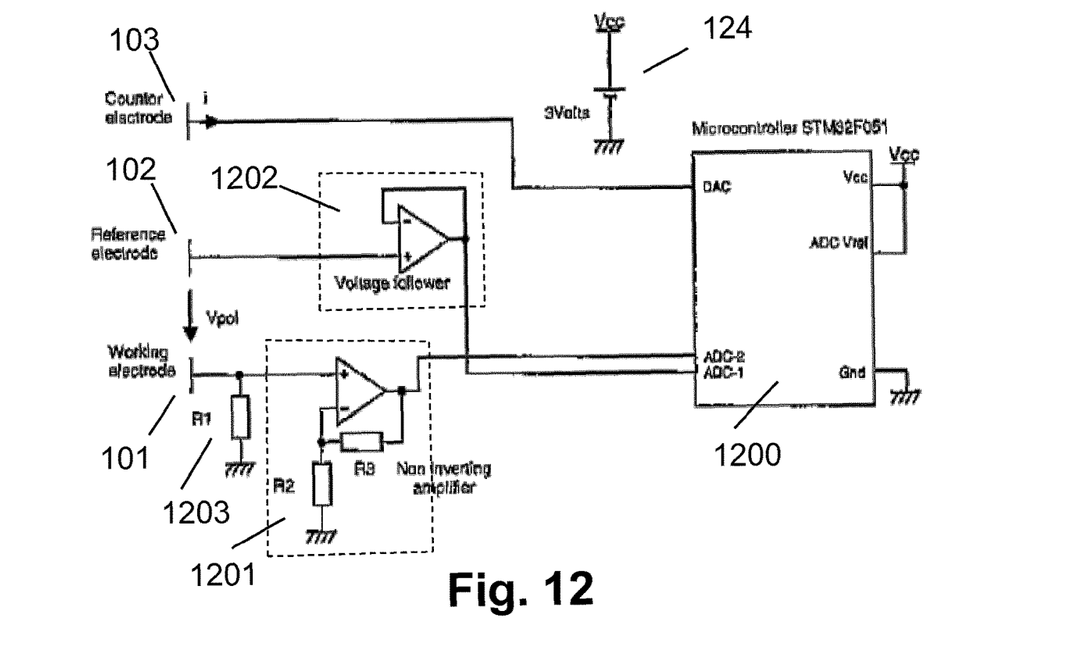
FIG. 12 shows a still further exemplary embodiment of a measurement and control circuit.

In the following, reference is additionally made to FIG. 12. FIG. 12 shows a further embodiment of the digital potentiostat circuit 120. The embodiment of FIG. 12 is designed for a negative polarization voltage and a negative current between working electrode 101 and counter electrode 103 and requires a particularly small number of components for this configuration. The embodiment of FIG. 12 is similar to the embodiment of FIG. 4. As sole difference, the role of control electrode and measurement electrode is reversed. In the embodiment of FIG. 4, the counter electrode 103 serves as measurement electrode and is coupled to the first analogue input ADC-2 via the non-inverting amplifier 1201. In the embodiment of FIG. 12, in contrast, the working electrode 101 serves as measurement electrode and is coupled to the first analogue input ADC-2 via the non-inverting amplifier 1201. Similarly, in the embodiment of FIG. 4, the working electrode 101 serves as control electrode and is directly coupled to the control output DAC. In the embodiment of FIG. 12, in contrast, the counter electrode 103 serves as control electrode and is directly coupled to the control output DAC.

In a variant, current is measured using a differential amplifier on either of the working electrode 101 or the counter electrode 103. In a further variant, the working electrode 101 serves as control electrode and the current is measured at the working electrode 101 or the counter electrode 103 using a differential amplifier.

As mentioned before, a—favorably passive—sample-and-hold unit may generally be used in the before-described embodiments in the coupling of control output and control electrode in order to reduce the energy consumption.

The invention claimed is:

1. Analyte measuring patch for invasively measuring a concentration of an analyte, the analyte measuring patch including:
   a sensor for transcutaneous placement in a patient's tissue, the sensor including a working electrode, a counter electrode and a reference electrode;
   a pad for placement on the patient's skin, wherein the sensor projects from an adhesive surface of the pad
   an electronics unit, wherein the electronics unit includes a microcontroller and a current measurement unit;
   wherein the microcontroller includes a digital-to-analogue converter (DAC) with a control output;
   wherein the microcontroller includes a first analogue input and a second analogue input;
   wherein the control output of the DAC is operatively coupled with a control electrode through a direct galvanic coupling, the direct galvanic coupling having a flow path without electronic components;

wherein the first analogue input is operatively coupled with a measurement electrode via the current measurement unit;

wherein the control electrode is one of the working electrode or the counter electrode, and the measurement electrode is the other of the working electrode or the counter electrode;

wherein the second analogue input is operatively coupled with the reference electrode;

wherein the microcontroller is configured to control, by providing a control voltage to the control output, a potential difference between the working electrode and the counter electrode to equal a pre-defined polarization voltage.

2. The analyte measuring patch according to claim 1, wherein the electronics unit includes a voltage follower and the reference electrode is operatively coupled to the second analogue input via the voltage follower.

3. The analyte measuring patch according to claim 1, wherein the current measurement unit includes a differential amplifier or a current-to-voltage converter.

4. The analyte measuring patch according to claim 1, wherein the control electrode is the counter electrode and the measurement electrode is the working electrode.

5. The analyte measuring patch according to claim 1, wherein the electronics unit is operatively coupled to or designed for operatively coupling to an asymmetric power supply.

6. The analyte measuring patch according to claim 1, wherein the microcontroller is configured to detect air bubbles in contact with at least one of the working electrode, the counter electrode and/or the reference electrode.

7. The analyte measuring patch according to claim 1, wherein the electronics unit and the sensor are non-detachably mechanically coupled.

8. The analyte measuring patch according to claim 1, wherein the sensor and the electronics unit are detachably mechanically coupled or designed to be detachably mechanically coupled.

9. The analyte measuring patch according to claim 1, wherein the electronics unit includes a data communication unit, the electronics unit being designed to exchange, via the data communication unit, data with a further electronics unit.

10. The analyte measuring patch according to claim 9, wherein the data communication unit is a wireless data communication unit, and wherein the electronics unit is sealed in a water tight manner.

11. The analyte measuring patch according to claim 10, wherein the wireless data communication unit is a near field communication unit.

12. The analyte measuring patch according to claim 9, wherein the further electronics unit includes a further data communication unit for operatively coupling with the data communication unit, the further electronics unit being designed to detachably mechanically couple to the electronics unit.

13. The analyte measuring patch according to claim 12, wherein the electronics unit and the further electronics unit each include separate power supplies.

14. The analyte measuring patch according to claim 9, wherein the data includes analyte concentration data or data correlated with analyte concentration.

15. The analyte measuring patch according to claim 9, wherein the electronics unit includes a coupling structure arranged and configured to releasably mechanically couple the further electronics unit to the electronics unit.

16. The analyte measuring patch according to claim 1, further including a wireless remote device communication unit, the wireless remote device communication unit being operatively coupled to the microcontroller and being designed to exchange data with a further separate remote device.

17. The analyte measuring patch according to claim 16, wherein the data includes analyte concentration data or data correlated with analyte concentration.

18. The analyte measuring patch according to claim 1, wherein the analyte includes glucose.

19. The analyte measuring patch according to claim 1, wherein the pad includes an interface structure extending away from the pad that is arranged and configured to releasably mechanically couple the electronics unit to the pad.

20. Analyte measuring patch for invasively measuring a concentration of an analyte, the analyte measuring patch including:
a sensor for transcutaneous placement in a tissue of a patient, the sensor including a working electrode, a counter electrode and a reference electrode;
a pad for placement on skin of the patient, wherein the sensor projects from an adhesive surface of the pad
an electronics unit, wherein the electronics unit includes a microcontroller and a current measurement unit;
wherein the microcontroller includes a digital-to-analogue converter (DAC) with a control output;
wherein the microcontroller includes a first analogue input and a second analogue input;
wherein the control output of the DAC is operatively coupled with the counter electrode through a direct galvanic coupling, the direct galvanic coupling having a flow path without electronic components;
wherein the first analogue input is operatively coupled with the working electrode via the current measurement unit;
wherein the second analogue input is operatively coupled with the reference electrode;
wherein the microcontroller is configured to control, by providing a control voltage to the control output, a potential difference between the working electrode and the counter electrode to equal a pre-defined polarization voltage.

* * * * *